(12) United States Patent
Yamada et al.

(10) Patent No.: US 8,580,405 B2
(45) Date of Patent: Nov. 12, 2013

(54) NAPHTHOTHIOPHENE COMPOUND AND ORGANIC LIGHT-EMITTING DEVICE INCLUDING THE SAME

(75) Inventors: Naoki Yamada, Inagi (JP); Jun Kamatani, Tokyo (JP); Akihito Saitoh, Gotemba (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/642,489

(22) PCT Filed: Apr. 11, 2011

(86) PCT No.: PCT/JP2011/059466
§ 371 (c)(1),
(2), (4) Date: Oct. 19, 2012

(87) PCT Pub. No.: WO2011/132623
PCT Pub. Date: Oct. 27, 2011

(65) Prior Publication Data
US 2013/0037789 A1 Feb. 14, 2013

(30) Foreign Application Priority Data
Apr. 22, 2010 (JP) .................. 2010-099152

(51) Int. Cl.
H01L 51/54 (2006.01)

(52) U.S. Cl.
USPC .......... 428/690; 428/917; 313/504; 313/505; 313/506; 257/40; 257/E51.05; 257/E51.026; 257/E51.032; 546/82; 546/87; 546/216; 548/440; 544/250; 544/333

(58) Field of Classification Search
USPC .................. 428/690, 917; 313/504, 505, 506; 257/40, E51.05, E51.026, E51.032; 546/82, 87, 216; 548/440; 544/250, 544/333
See application file for complete search history.

(56) References Cited

FOREIGN PATENT DOCUMENTS

| JP | 2009-203176 A | | 9/2009 |
|---|---|---|---|
| JP | 2009-203203 | * | 9/2009 |
| JP | 2009-203203 A | | 9/2009 |
| WO | 2008/143229 A1 | | 11/2008 |
| WO | 2010/036027 A2 | | 4/2010 |

* cited by examiner

*Primary Examiner* — Gregory Clark
(74) *Attorney, Agent, or Firm* — Canon U.S.A. Inc., IP Division

(57) ABSTRACT

The present invention provides a novel naphthothiophene compound having a high lowest excited triplet level (T1).

5 Claims, 1 Drawing Sheet

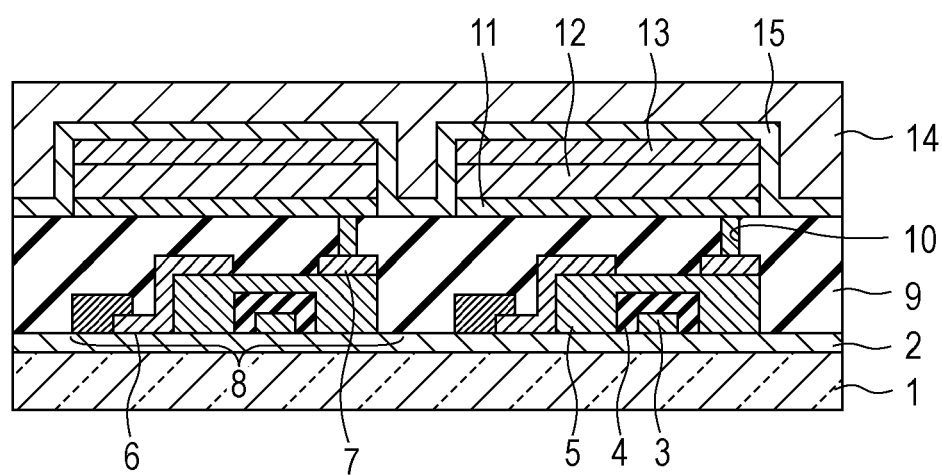

NAPHTHOTHIOPHENE COMPOUND AND ORGANIC LIGHT-EMITTING DEVICE INCLUDING THE SAME

TECHNICAL FIELD

The present invention relates to a novel naphthothiophene compound and an organic light-emitting device including the same.

BACKGROUND ART

An organic light-emitting device is a device including a pair of electrodes and an organic compound layer disposed therebetween. Electrons and holes are injected from the pair of electrodes to generate excitons of a luminescent organic compound in the organic compound layer, and light is emitted when the excitons return to the ground state.

PTL 1 and PTL 2 describe compounds A-1 and A-2 shown below, respectively, as an example of a naphthothiophene compound constituting a light-emitting layer.

[Chem. 1]

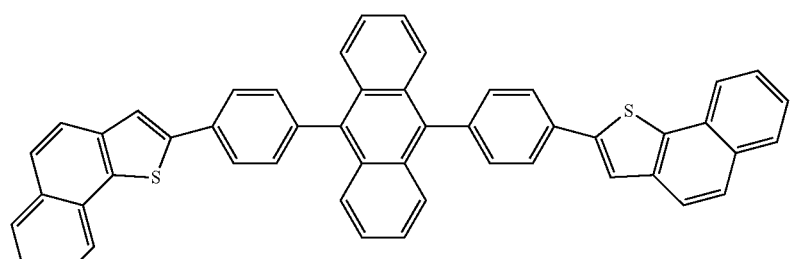

A-1

[Chem. 2]

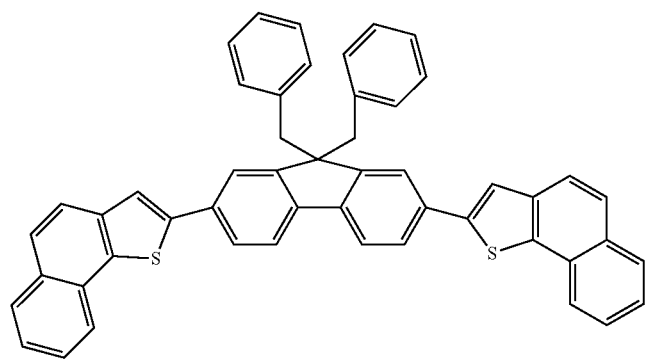

A-2

These compounds have, as a substituent, naphthothiophene shown below.

[Chem. 3]

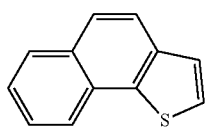

CITATION LIST

Patent Literature

PTL 1 Japanese Patent Laid-Open No. 2009-203203
PTL 2 Japanese Patent Laid-Open No. 2009-203176

SUMMARY OF INVENTION

Technical Problem

These compounds have a low lowest excited triplet level (T1).

The present invention provides a novel naphthothiophene compound having a high T1 value. The present invention also provides an organic light-emitting device having high luminous efficiency and a low driving voltage.

As the novel organic compound according to the present invention, there is provided an organic compound represented by general formula [1] shown below.

[Chem. 4]

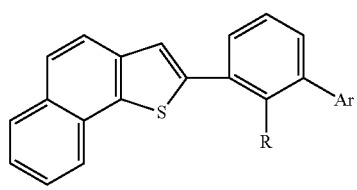

General formula [1]

In general formula [1], Ar represents any one of a phenyl group, a phenanthryl group, a naphthyl group, a fluorenyl group, and a triphenylenyl group, and may have, as a substituent, any one kind selected from alkyl groups having 1 to 4 carbon atoms, a phenyl group, a phenanthryl group, a naphthyl group, a fluorenyl group, and a triphenylenyl group. R represents a hydrogen atom or an alkyl group having 1 to 4 carbon atoms.

BRIEF DESCRIPTION OF DRAWINGS

FIG. 1 is a schematic cross-sectional view showing organic light-emitting devices and switching devices connected to the organic light-emitting devices.

DESCRIPTION OF EMBODIMENTS

A novel organic compound according to the present invention is a naphthothiophene compound represented by general formula [1] shown below:

[Chem. 5]

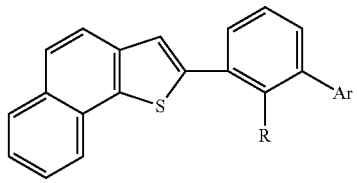

General formula [1]

In general formula [1], Ar represents any one of a phenyl group, a phenanthryl group, a naphthyl group, a fluorenyl group, and a triphenylenyl group. R represents a hydrogen atom or an alkyl group having 1 to 4 carbon atoms.

Specific examples of the alkyl group having 1 to 4 carbon atoms of R in general formula [1] include a methyl group, an ethyl group, an n-propyl group, an iso-propyl group, an n-butyl group, an iso-butyl group, a sec-butyl group, and a tert-butyl group.

Ar in general formula [1] may have a substituent. The substituent is any one kind selected from alkyl groups having 1 to 4 carbon atoms, a phenyl group, a phenanthryl group, a naphthyl group, a fluorenyl group, and a triphenylenyl group. That is, Ar may have a plurality of substituents of the same kind. Specific examples of the alkyl group having 1 to 4 carbon atoms as the substituent include a methyl group, an ethyl group, an n-propyl group, an iso-propyl group, an n-butyl group, an iso-butyl group, a sec-butyl group, and a tert-butyl group.

The naphthothiophene compound according to the present invention has both of the following two characteristics:
(1) The lowest excited triplet level (T1) is in the range of 460 to 500 nm. That is, T1 is high.
(2) The hole mobility and the electron mobility are high.
Description of Item (1)

In the naphthothiophene compound according to the present invention, as shown in general formula [1], the naphthothiophene group and the aryl group represented by Ar are bound to the 1-position and the 3-position of the phenylene group, respectively. Consequently, this compound has a structure in which the naphthothiophene group and the aryl group are not conjugated. The 1- and 3-positions of the phenylene group refer to the positions shown below.

[Chem. 6]

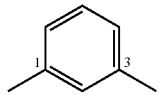

The 1- and 4-positions of the phenylene group refer to the positions shown below.

[Chem. 7]

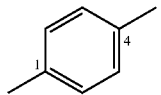

The structure in which the naphthothiophene group and the aryl group are bound to the 1-position and the 3-position of the phenylene group, respectively, means that the compound represented by general formula [1] maintains the T1 value (466 nm as measured in Example 1) of the naphthothiophene group itself.

Table 1 below shows the T1 values of various compounds constituted by the naphthothiophene group, the aryl group, and the phenylene group, calculated by the molecular orbital method.

Furthermore, according to Example 1, the measured T1 value of compound I-7 is 471 nm. From this, it is assumed that the error between the calculated value and the measured value in a dilute toluene solution is several nanometers in any of the compounds.

In the molecular orbital calculations, the most stabilized structures were obtained using the technique described below.

In the molecular orbital calculations, the calculation technique of DFT basis function 6-31+G(d) was used in Gaussian 03 (Gaussian 03, Revision D.01, M. J. Frisch, G. W. Trucks, H. B. Schlegel, G. E. Scuseria, M. A. Robb, J. R. Cheeseman, J. A. Montgomery, Jr., T. Vreven, K. N. Kudin, J. C. Burant, J. M. Millam, S. S. Iyengar, J. Tomasi, V. Barone, B. Mennucci, M. Cossi, G. Scalmani, N. Rega, G. A. Petersson, H. Nakatsuji, M. Hada, M. Ehara, K. Toyota, R. Fukuda, J. Hasegawa, M. Ishida, T. Nakajima, Y. Honda, O. Kitao, H. Nakai, M. Klene, X. Li, J. E. Knox, H. P. Hratchian, J. B. Cross, V. Bakken, C. Adamo, J. Jaramillo, R. Gomperts, R. E. Stratmann, O. Yazyev, A. J. Austin, R. Cammi, C. Pomelli, J. W. Ochterski, P. Y. Ayala, K. Morokuma, G. A. Voth, P. Salvador, J. J. Dannenberg, V. G. Zakrzewski, S. Dapprich, A. D. Daniels, M. C. Strain, O. Farkas, D. K. Malick, A. D. Rabuck, K. Raghavachari, J. B. Foresman, J. V. Ortiz, Q. Cui, A. G. Baboul, S. Clifford, J. Cioslowski, B. B. Stefanov, G. Liu, A. Liashenko, P. Piskorz, I. Komaromi, R. L. Martin, D. J. Fox, T. Keith, M. A. Al-Laham, C. Y. Peng, A. Nanayakkara, M. Challacombe, P. M. W. Gill, B. Johnson, W. Chen, M. W. Wong, C. Gonzalez, and J. A. Pople, Gaussian, Inc., Wallingford Conn., 2004).

TABLE 1
Comparison of calculated T1 values
| Exemplary compound No. | T1 nm (calculated value) |
|---|---|
| I-7 | 475 |
| H-1 | 494 |
| B-1 | 512 |
| B-2 | 515 |
| B-3 | 513 |
TABLE 1-continued
Comparison of calculated T1 values
| Exemplary compound No. | T1 nm (calculated value) |
|---|---|
| A-1 | 715 |
| A-2 | 559 |
The structural formulae of the compounds in the table are as follows:
[Chem. 8]
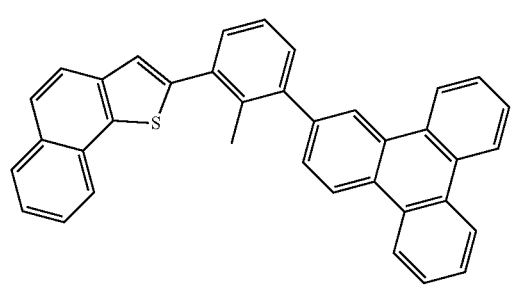
I-7
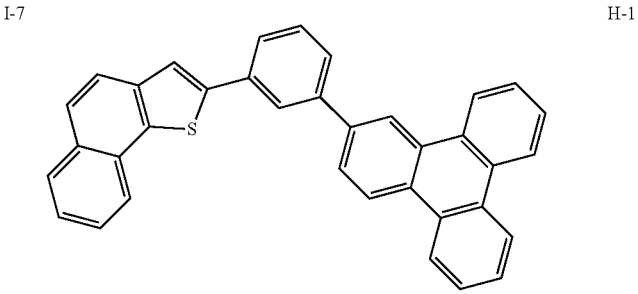
H-1
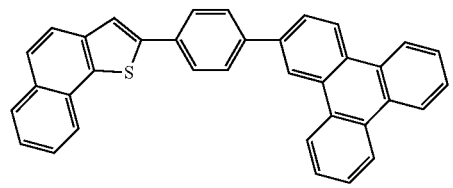
B-1
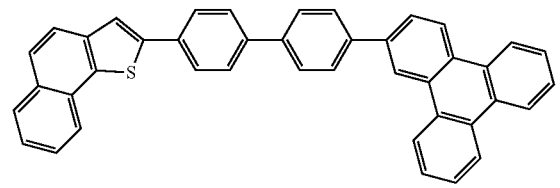
B-2
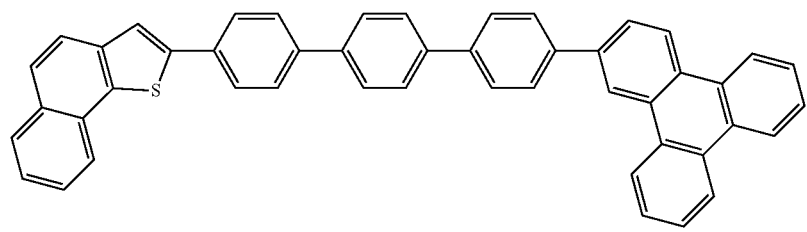
B-3
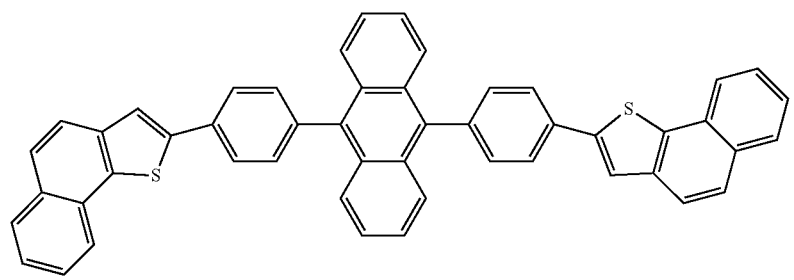
A-1

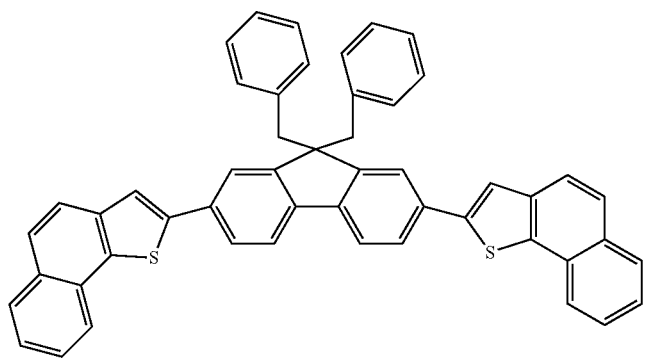

A-2

When the calculation results are compared, compounds I-7 and H-1 each have a structure in which the naphthothiophene group and the aryl group are bound to the 1-position and the 3-position of the phenylene group, and the T1 value is close to the T1 value of the naphthothiophene itself and is 500 nm or less.

Meanwhile, compound B-1 has a structure in which the naphthothiophene group and aryl group are bound to the 1-position and the 4-position of the phenylene group. Since the naphthothiophene group and the aryl group are conjugated, T1 is lower than that of the structure in which binding occurs to the 1-position and the 3-position of the phenylene group, and the T1 value is 500 nm or more. Furthermore, compounds B-2 and B-3 each have a structure in which two or three phenylene groups are bound, and the naphthothiophene group and the aryl group are bound to the 1-position and the 4-position of the phenylene group. Therefore, the T1 value is 500 nm or more.

In compounds A-1 and A-2, similarly, the T1 value is more than 500 nm.

The naphthothiophene compound according to the present invention has a T1 value of 460 to 500 nm, and thus has high energy. A phosphorescent compound that emits green phosphorescence has a T1 value of 500 to 520 nm, and the naphthothiophene compound according to the present invention has a higher T1 energy than the phosphorescent compound that emits green phosphorescence. Consequently, the naphthothiophene compound according to the present invention can be used suitably as a host material for the light-emitting layer of an organic light-emitting device that emits green phosphorescence. In this case the compound that emits green phosphorescence is a guest material for the light-emitting layer.

Description of Item (2)

Since the naphthothiophene compound according to the present invention has the naphthothiophene group, it has high hole mobility. Specifically, the hole mobility is in the range of $1.0 \times 10^{-3}$ to $1.0 \times 10^{-5}$ $cm^2 V^{-1} s^{-1}$. In addition, since the naphthothiophene compound has the aryl group, it has high electron mobility. Specifically, the electron mobility is in the range of $1.0 \times 10^{-3}$ to $1.0 \times 10^{-5}$ $cm^2 V^{-1} s^{-1}$.

The phenyl group, the phenanthryl group, the naphthyl group, the fluorenyl group, and the triphenylenyl group, which are shown as examples of Ar, each have high electron mobility, and thus are preferable. The fluorenyl group and the triphenylenyl group are more preferable.

The naphthothiophene compound according to the present invention has high mobility of carriers, both holes and electrons. In the case where the compound according to the present invention is used for the organic layer in an organic light-emitting device, the driving voltage of the organic light-emitting device can be decreased, and thus the compound is suitable for the organic light-emitting device.

Exemplification of Organic Compounds According to the Present Invention

Specific examples of the compound represented by general formula (1) will be shown below. However, it is to be understood that the present invention is not limited thereto.

[Chem. 9]

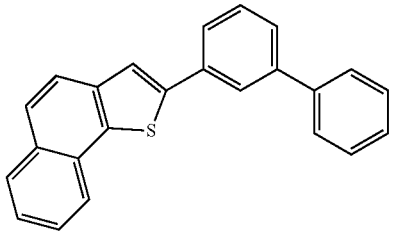

D-1

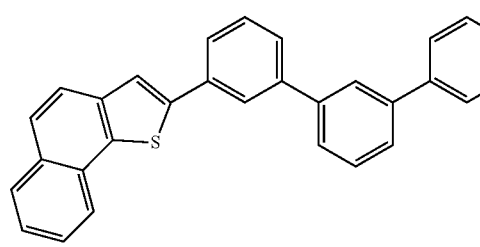

D-2

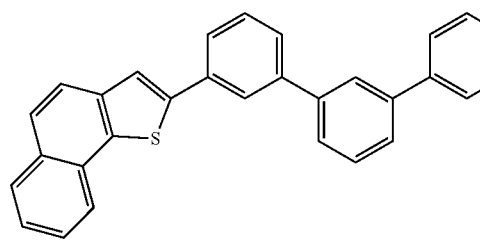

D-3

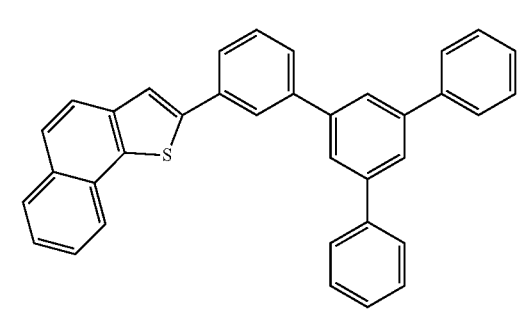
D-4
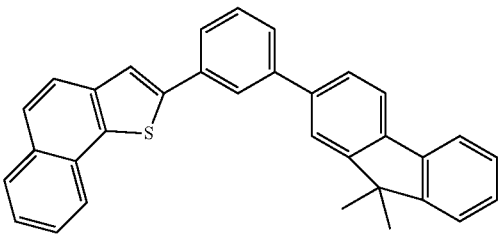
E-2
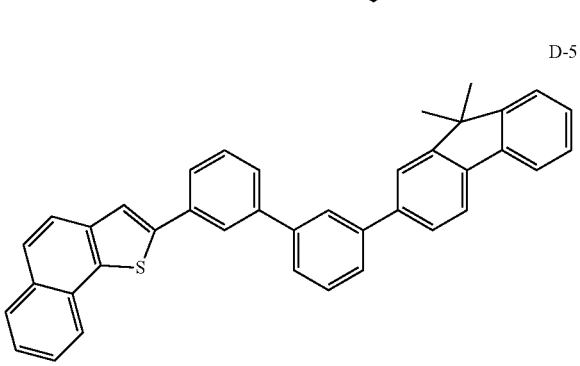
D-5
[Chem.10]
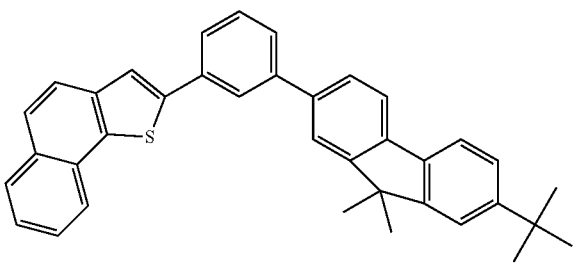
E-3
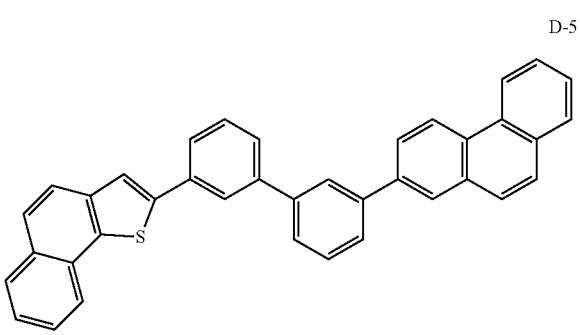
D-5
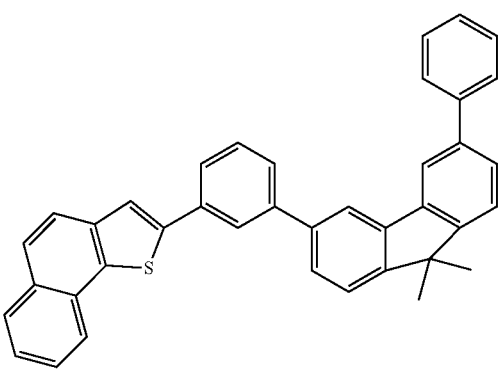
E-3
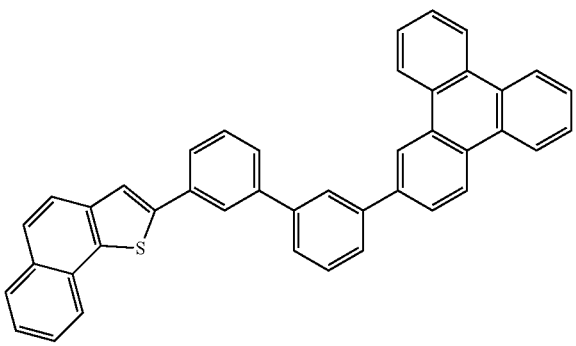
D-5
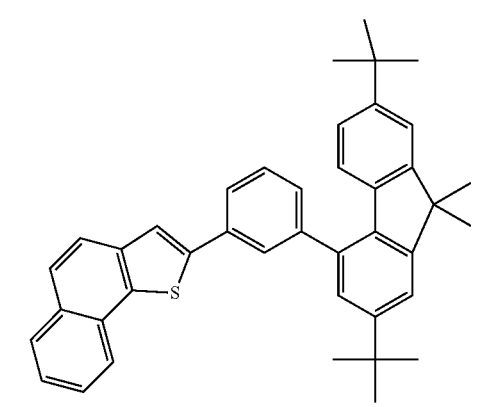
E-4
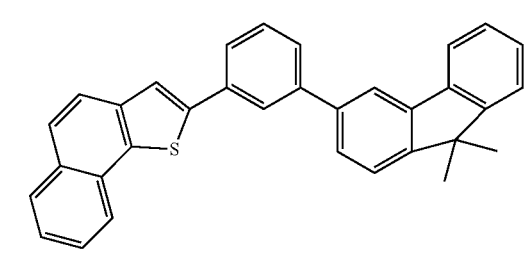
E-1
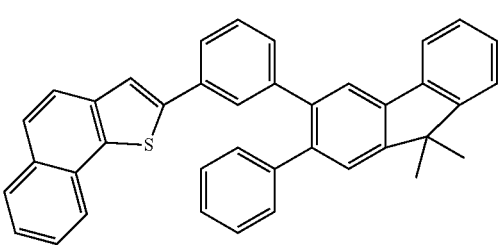
E-5

F-1
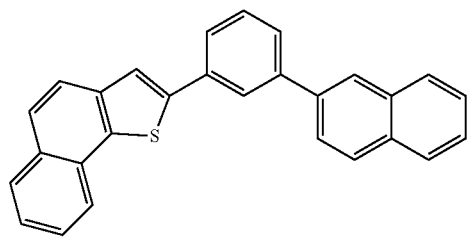
F-2
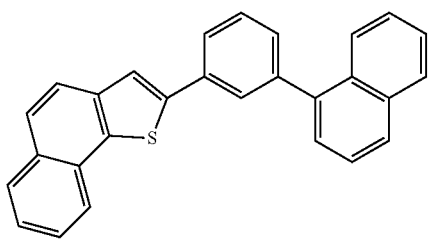
F-3
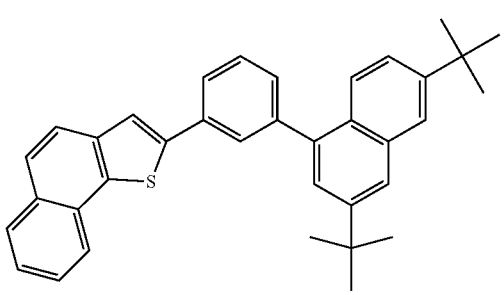
G-1
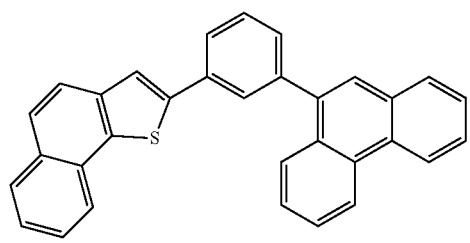
G-2
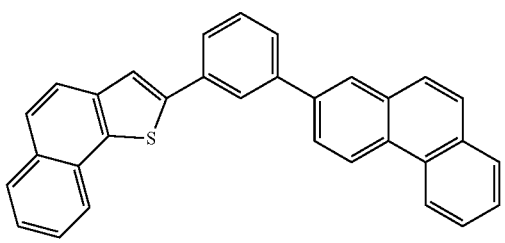
G-3
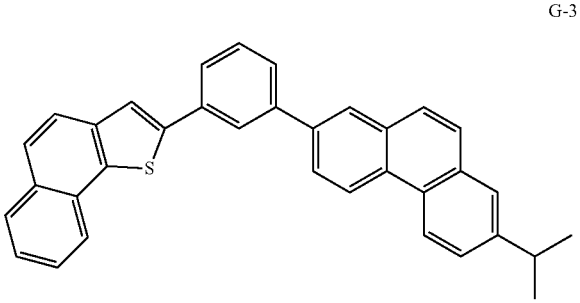
G-4
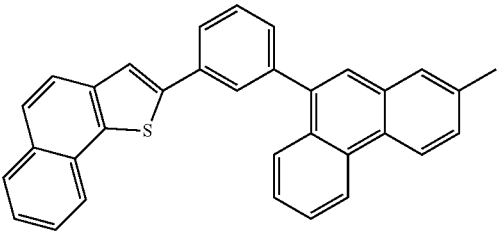
G-5
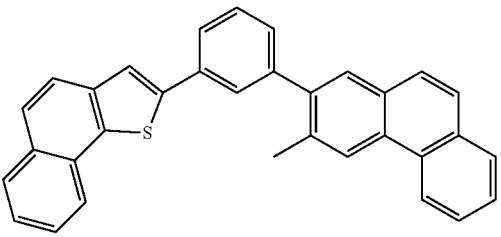
G-6
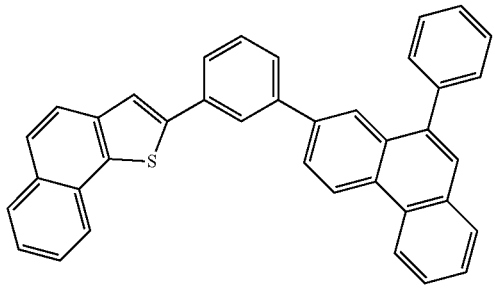
[Chem. 11]
H-1
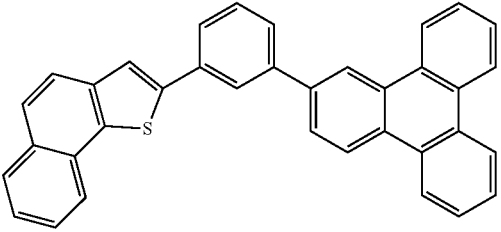
H-2
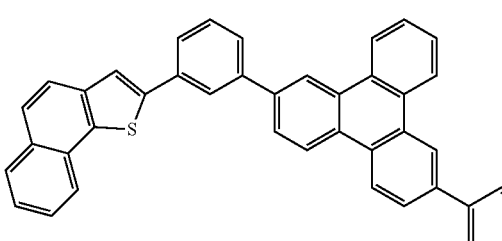
H-2
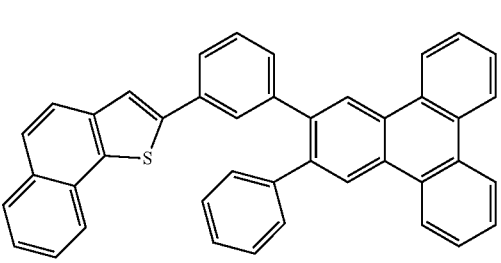

I-1 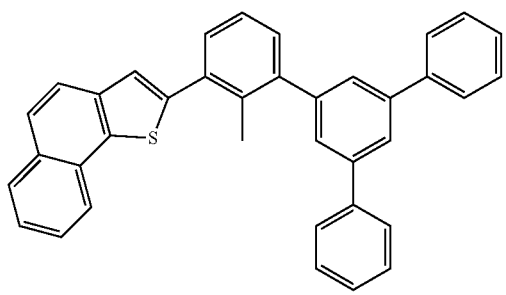

I-2 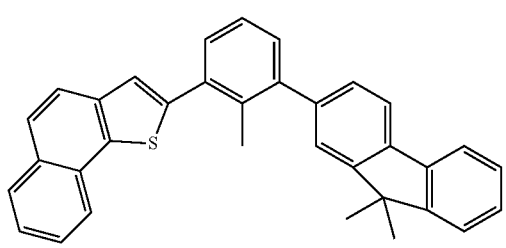

I-3 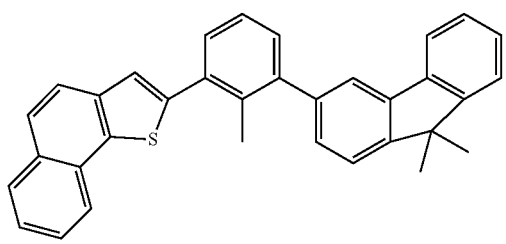

I-4 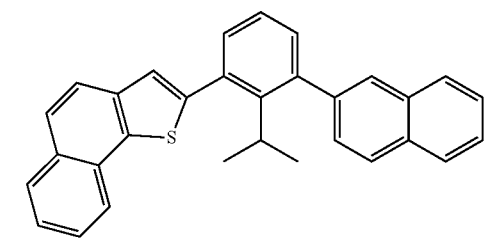

I-5 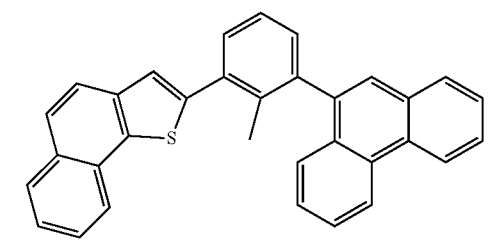

I-6 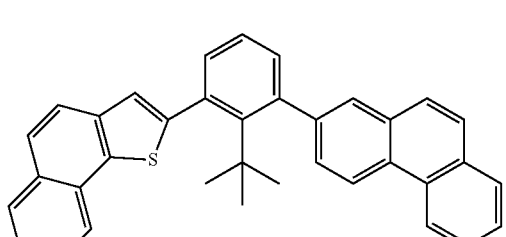

I-7 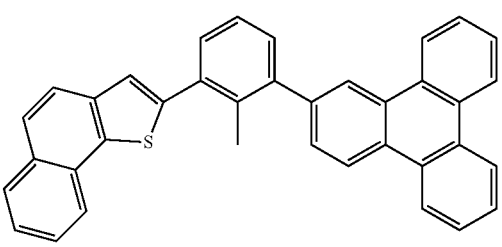

I-8 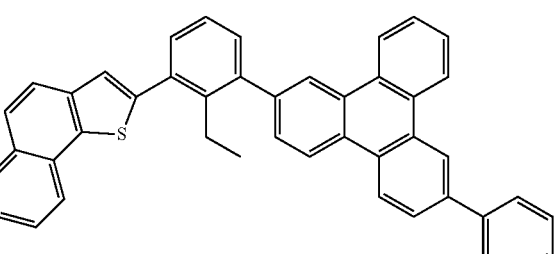

I-9 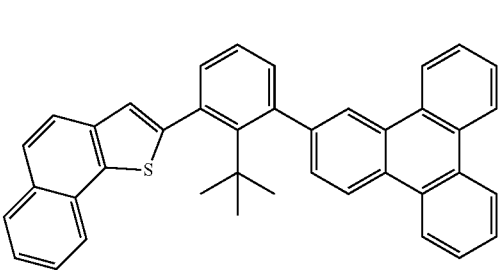

Properties of Exemplary Compounds

Table 2 shows the calculated T1 values of some of the exemplary compounds shown above. The calculations are made in the same manner as in Table 1.

The compounds represented by general formula [1] in which the phenyl group, the phenanthryl group, the naphthyl group, the fluorenyl group, or the triphenyl group is substituted as Ar have a T1 value in the range of 460 to 500 nm.

TABLE 2

| Exemplary compound No. | T1 nm (calculated value) |
| --- | --- |
| I-7 | 475 |
| I-1 | 474 |
| I-2 | 473 |
| I-4 | 474 |
| I-6 | 474 |

In compound groups D, E, F, G, and H, R represents a hydrogen atom in general formula [1]. The compounds in these compound groups have a structure in which the naphthothiophene group, the Ar group, and the central phenyl group maintain planarity. Therefore, the compounds have high hole and electron mobility.

In compound groups E and H, Ar in general formula [1] represents a fluorenyl group or a triphenylenyl group. Among compound groups D, E, F, G, and H, the compounds in compound groups E and H having a fluorenyl group or a triphenylenyl group as the Ar group particularly have high electron mobility. The reason for this is that the high electron mobility of the fluorenyl skeleton or the triphenylene skeleton is reflected.

In compound group D, Ar in general formula [1] represents a phenyl group.

In the compounds in this compound group, since the number of rotating sites in the molecule is large, the sublimation temperature is low, and the vapor deposition temperature in the organic light-emitting device fabrication process is low.

In compound groups F and G, Ar in general formula [1] represents a naphthyl group or a phenanthryl group. The compounds in these compound groups have high glass transition temperature.

In compound group I, R in general formula [1] represents an alkyl group having 1 to 4 carbon atoms.

In the compounds in this compound group, because of steric repulsion of the naphthothiophene group and the Ar group from the alkyl group-containing phenyl group, conjugation between molecules is broken, leading to higher T1. According to calculations shown in Table 1, the T1 value is 475 nm in 1-7 and 494 nm in H-1, indicating that the alkyl group has the effect of increasing T1.

Furthermore, steric repulsion of the naphthothiophene group and the Ar group from the alkyl group-containing phenyl group forms a structure in which molecular planarity is disturbed. Therefore, intermolecular association is suppressed, thus suppressing concentration quenching.

Description of Synthesis Route

An example of a synthesis route of the organic compound according to the present invention will be described. A reaction formula is described below.

An intermediate a-6 which is the basic skeleton of the naphthothiophene group can be synthesized by a coupling reaction between bromothiophene a-2 and benzaldehyde boronic acid a-1, a carbon elongation reaction using the Wittig reaction, and a cyclization reaction by an acid catalyst.

Bromides and pinacol boronates can be derived from the intermediate a-6, bromides and pinacol boronates being effective as starting materials for the synthesis of various naphthothiophene compounds represented by general formula [1].

Using a pinacol boronate, a benzene derivative a-9, and a pinacol boronate derivative a-11, a naphthothiophene compound a-12 represented by general formula [1] can be synthesized.

Furthermore, the intermediate a-9 may be a halide other than a bromide or a triflate, and the intermediate a-11 may be a boronate. In this case, synthesis can be carried out in the same manner.

[Chem. 12]

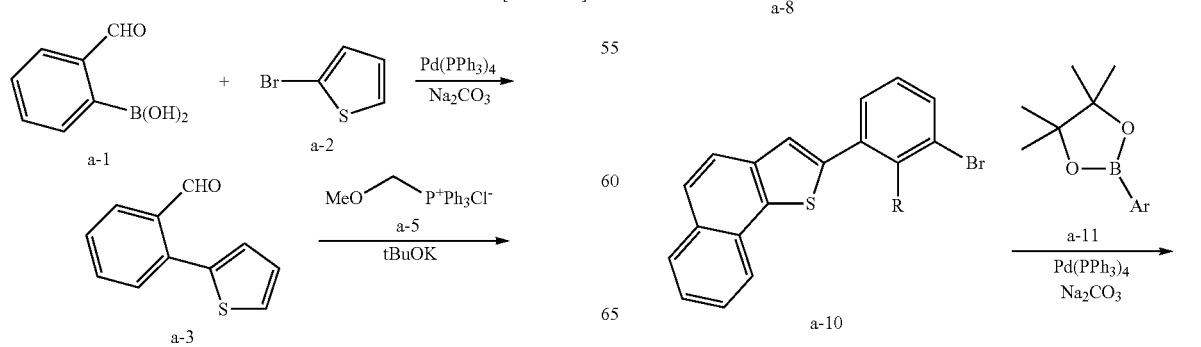

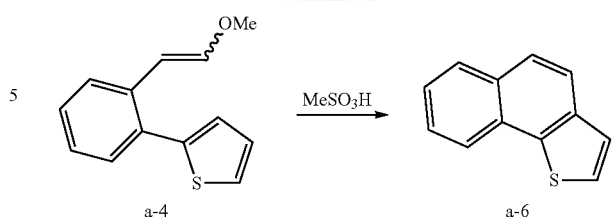

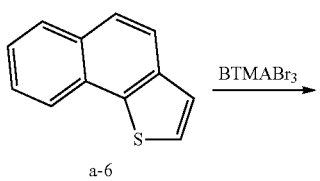

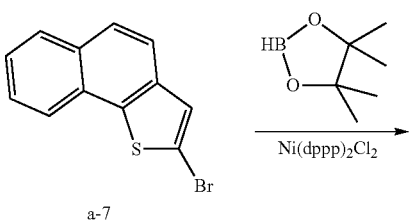

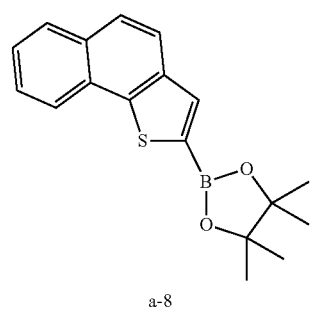

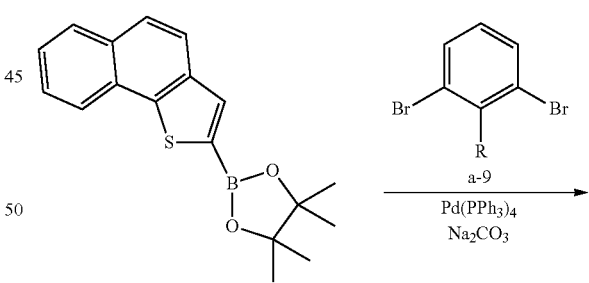

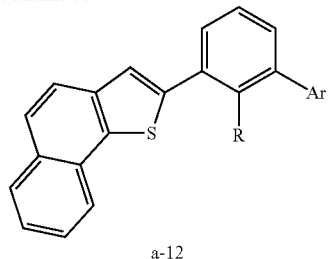

a-12

Description of Organic Light-Emitting Device

An organic light-emitting device according to an embodiment of the present invention will now be described.

The organic light-emitting device according to the embodiment includes a pair of electrodes, i.e., an anode and a cathode, and an organic compound layer disposed between the electrodes. The organic compound layer includes an organic compound represented by general formula [1].

Examples of the structure of an organic light emitting device fabricated using the organic compound according to the present invention include a structure in which an anode, a light-emitting layer, and a cathode are disposed in that order on a substrate; a structure in which an anode, a hole transport layer, an electron transport layer, and a cathode are disposed in that order; a structure in which an anode, a hole transport layer, a light-emitting layer, an electron transport layer, and a cathode are disposed in that order; a structure in which an anode, a hole injection layer, a hole transport layer, a light-emitting layer, an electron transport layer, and a cathode are disposed in that order; and a structure in which an anode, a hole transport layer, a light-emitting layer, a hole/exciton blocking layer, an electron transport layer, and a cathode are disposed in that order. However, it is to be understood that these five multilayer structures are merely basic device structures, and the structure of the organic light-emitting device using the compound according to the present invention is not limited thereto.

The organic compound represented by general formula [1] according to the present invention can be used as a host material or a guest material of a light-emitting layer. In particular, when the organic compound is used as a phosphorescent host material and the host material is combined with a guest material that emits light in the green to red regions with an emission peak in the range of 490 to 660 nm, the loss of triplet energy is small, and therefore, efficiency of the light emitting device is high.

When the organic compound according to the embodiment is used as a guest material, the concentration of the guest material relative to the host material is preferably 0.1% to 30% by mass, and more preferably 0.5% to 10% by weight.

Furthermore, the organic compound represented by general formula [1] according to the present invention can be used for an electron blocking layer or a hole transport layer. The organic compound represented by general formula [1] has high hole transport properties because of the naphthothiophene group and has an electron injection level that is sufficiently high to block electrons from the light-emitting layer. Therefore, it is possible to provide an organic light-emitting device which is driven with a low voltage and which emits light with high efficiency.

In the organic light-emitting device according to the embodiment, in addition to the organic compound according to the present invention, a hole-injecting material or hole-transporting material, a host material or guest material, an electron-injecting material or electron-transporting material, or the like can be appropriately used together. These materials may be low-molecular compounds or high-molecular compounds.

Examples of these compounds will be described below.

As the hole-injecting material or hole-transporting material, a material having high hole mobility is suitable. Examples of low-molecular and high-molecular materials having hole injection ability or hole transport ability include, but are not limited to, triarylamine derivatives, phenylenediamine derivatives, stilbene derivatives, phthalocyanine derivatives, porphyrin derivatives, poly(vinylcarbazole), poly(thiophene), and other conductive polymers.

Examples of the host material include, but are not limited to, triarylamine derivatives, phenylene derivatives, fused-ring aromatic compounds (e.g., naphthalene derivatives, phenanthrene derivatives, fluorene derivatives, chrysene derivatives, and the like), organometallic complexes (e.g., organoaluminum complexes such as tris(8-quinolinolato)aluminum, organoberyllium complexes, organoiridium complexes, and organoplatinum complexes), and polymer derivatives such as poly(phenylene vinylene) derivatives, poly(fluorene) derivatives, poly(phenylene) derivatives, poly(thienylene vinylene) derivatives, and poly(acetylene) derivatives.

Examples of the guest material include phosphorescent Ir complexes shown below and platinum complexes.

[Chem.13]

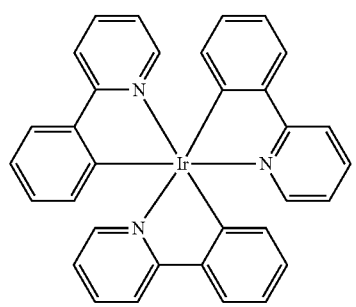

K-1

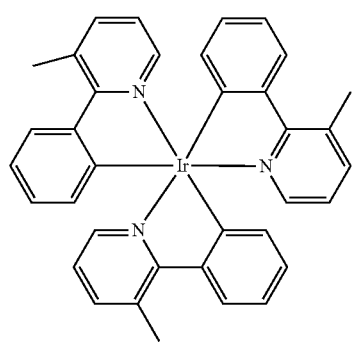

K-2

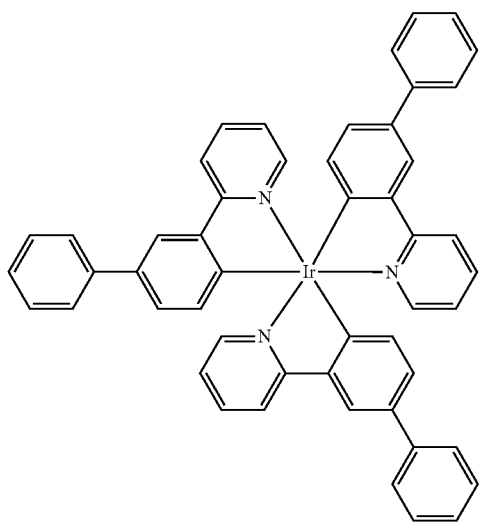

K-3

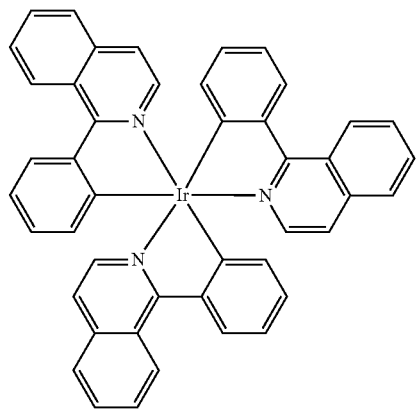

K-4

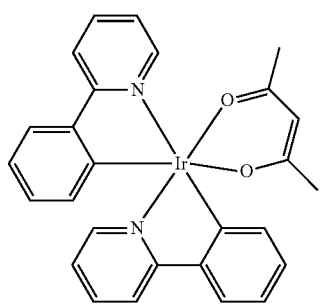

K-5

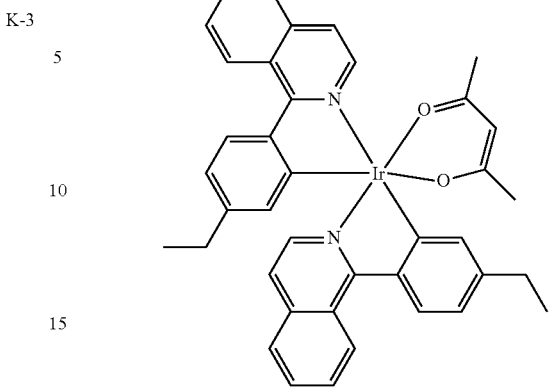

K-6

Furthermore, a fluorescent dopant can also be used. Examples thereof include fused-ring compounds (e.g., fluorene derivatives, naphthalene derivatives, pyrene derivatives, perylene derivatives, tetracene derivatives, anthracene derivatives, rubrene, and the like), quinacridone derivatives, coumarin derivatives, stilbene derivatives, organoaluminum complexes such as tris(8-quinolinolato)aluminum, organoberyllium complexes, and polymer derivatives such as poly(phenylene vinylene) derivatives, poly(fluorene) derivatives, and poly(phenylene) derivatives.

The electron-injecting material or electron-transporting material is selected taking into consideration the balance with the hole mobility of the hole-injecting material or hole-transporting material. Examples of the material having electron injection ability or electron transport ability include, but are not limited to, oxadiazole derivatives, oxazole derivatives, pyrazine derivatives, triazole derivatives, triazine derivatives, quinoline derivatives, quinoxaline derivatives, phenanthroline derivatives, and organoaluminum complexes.

A material having a work function that is as large as possible can be used as the material for the anode. Examples thereof include elemental metals, such as gold, platinum, silver, copper, nickel, palladium, cobalt, selenium, vanadium, and tungsten; alloys of these elemental metals; and metal oxides, such as tin oxide, zinc oxide, indium oxide, indium tin oxide (ITO), and indium zinc oxide. Furthermore, conductive polymers, such as polyaniline, polypyrrole, and polythiophene, may be used. These electrode materials may be used alone or in combination of two or more. The anode may include a single layer or multiple layers.

A material having a small work function can be used as the material for the cathode. Examples thereof include elemental metals, such as alkali metals (e.g., lithium), alkaline-earth metals (e.g., calcium), aluminum, titanium, manganese, silver, lead, and chromium. Alloys of these elemental metals can also be used. For example, magnesium-silver, aluminum-lithium, aluminum-magnesium, and the like can be used. Metal oxides, such as indium tin oxide (ITO), can also be used. These electrode materials may be used alone or in combination of two or more. The cathode may include a single layer or multiple layers.

In the organic light-emitting device according to the embodiment, layers containing the organic compounds according to the embodiment and layers containing other organic compounds are formed by the method described below. In general, layers are formed by vacuum vapor deposition, ionized vapor deposition, sputtering, a plasma method, or a known application method (e.g., spin coating, dipping, casting, an LB method, an ink jet method, or the like) using an appropriate solvent solution. When layers are formed by vacuum vapor deposition, the solution application method, or the like, crystallization or the like does not easily occur, and excellent stability with time is exhibited. When layers are formed by the application method, the layers can be formed by combining an appropriate binder resin with the organic compounds.

Examples of the binder resin include, but are not limited to, a polyvinyl carbazole resin, a polycarbonate resin, a polyester resin, an ABS resin, an acrylic resin, a polyimide resin, a phenolic resin, an epoxy resin, a silicone resin, and a urea resin. These binder resins may be used alone as a homopolymer or as a mixture of two or more as a copolymer. Furthermore, as necessary, known additives, such as a plasticizer, an antioxidant, an ultraviolet absorber, and the like may also be used together.

Use of Organic Light-Emitting Device

The organic light-emitting device according to the present invention can be used for a display apparatus and an illumination apparatus. Other uses include an exposure light source of an electrophotographic image forming apparatus, a backlight of a liquid crystal display apparatus, and the like.

The display apparatus includes the organic light-emitting device according to the embodiment provided in a display. The display includes a plurality of pixels. Each pixel includes the organic light-emitting device according to the embodiment and a TFT device, which is an example of a switching device for controlling luminance, and an anode or a cathode of the organic light-emitting device is connected to a drain electrode or a source electrode of the TFT device. The display apparatus can be used as an image display apparatus of PC or the like.

The display apparatus may be an image output device having an image input portion to which information from an area CCD, a linear CCD, a memory card, or the like is input and configured to output the input image to a display. Furthermore, as a display included in an image pickup apparatus or an ink jet printer, the display apparatus may have both an image output function of displaying an image on the basis of image information input from the outside and an input function of inputting image processing information as an operation panel. Furthermore, the display apparatus may be used as a display of a multifunctional printer.

A display apparatus including an organic light-emitting device according to the embodiment will now be described with reference to FIG. 1.

FIG. 1 is a schematic cross-sectional view showing organic light-emitting devices according to the embodiment and TFT devices, as an example of switching devices, which are connected to the organic light-emitting devices. In FIG. 1, an organic light-emitting device and a TFT device constitute one unit, and two units are shown. Details of the structure will be described below.

A display apparatus shown in FIG. 1 includes a substrate 1 composed of glass or the like and a moisture-proof film 2 provided on the substrate 1 in order to protect TFT devices or organic compound layers. Reference numeral 3 denotes a gate electrode composed of a metal. Reference numeral 4 denotes a gate-insulating film, and reference numeral 5 denotes a semiconductor layer.

A TFT device 8 includes the semiconductor layer 5, a drain electrode 6, and a source electrode 7. An insulating film 9 is provided on the TFT device 8. An anode 11 of the organic light-emitting device is connected to the source electrode 7 through a contact hole 10. The structure of the display apparatus is not limited to this as long as one of the anode and the cathode is connected to one of the source electrode and the drain electrode of the TFT device.

In FIG. 1, a multiple-layered organic compound layer 12 is shown as a single layer. A first protective layer 14 and a second protective layer 15 are provided on a cathode 13 in order to suppress degradation of the organic light-emitting device.

In the display apparatus according to the embodiment, the switching device is not particularly limited. A single-crystal silicon substrate, an MIM device, an a-Si type device, or the like may be used.

EXAMPLES

The present invention will now be described in detail on the basis of examples. It is to be understood that the present invention is not limited thereto.

Example 1

Synthesis of Exemplary Compound I-7

Synthesis was carried out according to the synthesis scheme shown below.

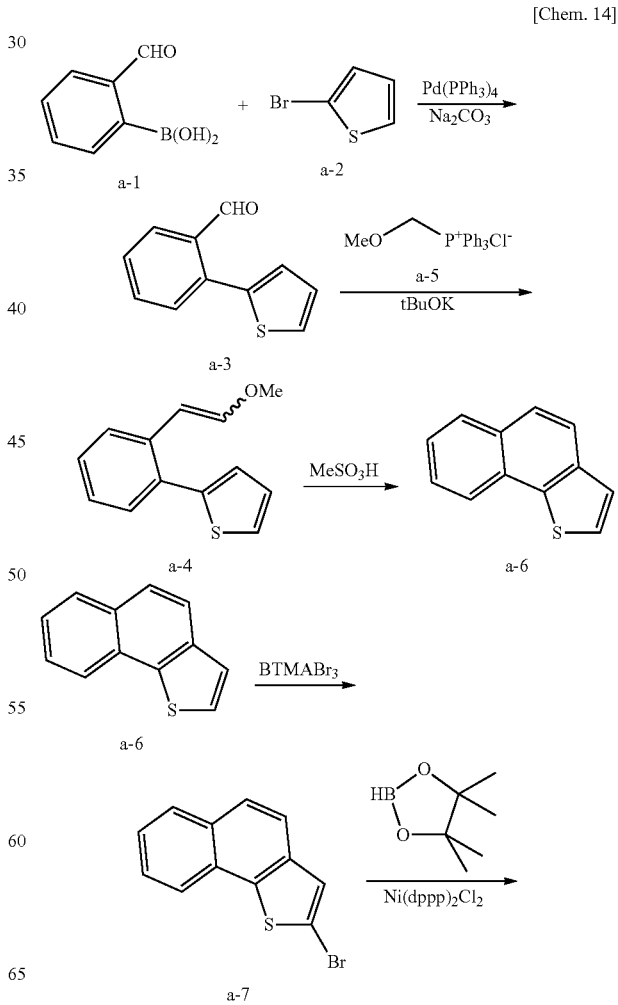

[Chem. 14]

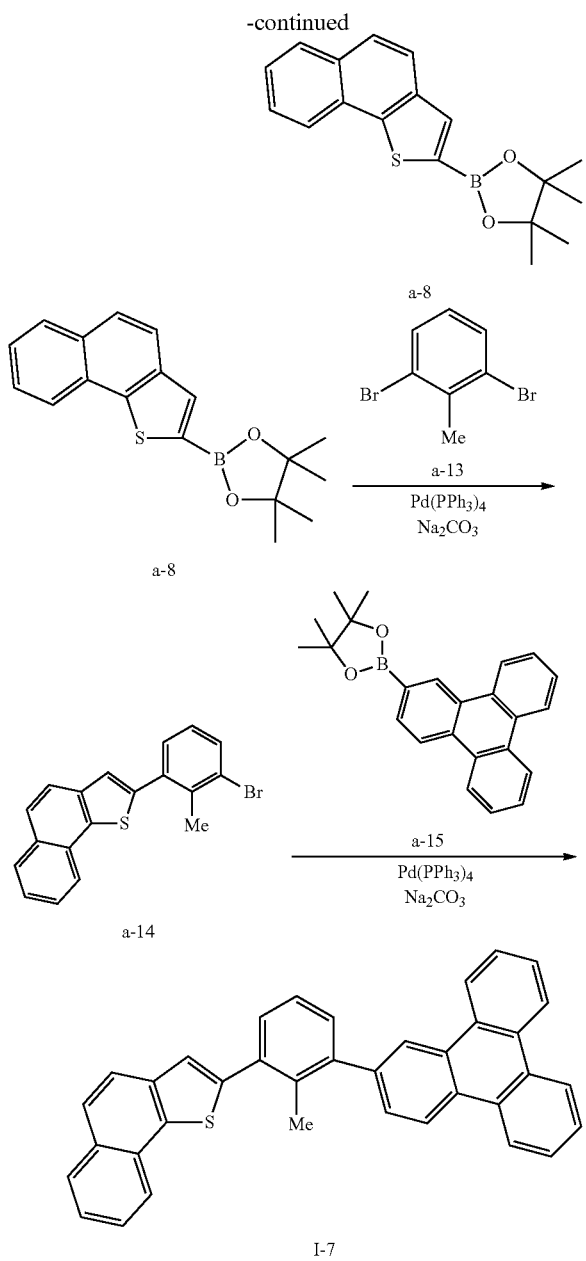

Synthesis of Intermediate a-3

In a 100-ml three-neck flask, 3.0 g (20 mmol) of compound a-1, 4.24 g (26 mmol) of compound a-2, 10.6 g (100.0 mmol) of sodium carbonate, 30 ml of toluene, 10 ml of ethanol, and 20 ml of water were placed, and in a nitrogen atmosphere, under stirring at room temperature, 693 mg of tetrakis(triphenylphosphine)palladium(0) was added thereto. The resulting mixture was heated to 80° C., and stirring was performed for 5 hours. After completion of the reaction, the organic layer was extracted with toluene and dried over anhydrous sodium sulfate, followed by purification by silica gel column chromatography (developing solvent: toluene/heptane mixture) to give 3.46 g (yield 92%) of intermediate a-3 (white oil).

Synthesis of Intermediate a-4

In a nitrogen atmosphere, 13.6 g (39.8 mmol) of compound a-5 was dissolved in 100 ml of tetrahydrofuran in a 200-ml three-neck flask, and under cooling with ice, 4.46 g (39.8 mmol) of tert-butoxy potassium was gradually added thereto. After stirring one hour, a solution obtained by dissolving 3.0 g (15.9 mmol) of intermediate a-3 in 20 ml of tetrahydrofuran was added dropwise to the mixture. Then, the reaction solution was heated to room temperature, and stirred for 5 hours. After completion of the reaction, the reaction solution was poured into 100 ml of water, and the organic layer was extracted with toluene and dried over anhydrous sodium sulfate, followed by purification by silica gel column chromatography (developing solvent: toluene/heptane mixture) to give 3.10 g (yield 91%) of intermediate a-4 (white solid).

Synthesis of Intermediate a-6

In a nitrogen atmosphere, 3.0 g (13.9 mmol) of compound a-4 and 50 ml of dichloromethane were placed in a 100-ml three-neck flask, and under cooling with ice, 1.35 ml (20.8 mmol) of methanesulfonic acid was added dropwise to the mixture. Then, the reaction solution was heated to room temperature, and stirred for 6 hours. After completion of the reaction, the reaction solution was poured into 100 ml of water, and the organic layer was extracted with chloroform and dried over anhydrous sodium sulfate, followed by purification by silica gel column chromatography (developing solvent: toluene/heptane mixture) to give 2.35 g (yield 91.8%) of intermediate a-6 (transparent oil).

Synthesis of Intermediate a-7

In a 100-ml three-neck flask, 2.30 g (12.48 mmol) of compound a-6, 5.35 g (13.73 mmol) of benzyltrimethylammonium tribromide, and 60 ml of chloroform were placed, and stirring was performed for 3 hours at room temperature. After completion of the reaction, 100 ml of water was added to the reaction solution, and the organic layer was extracted with toluene and dried over anhydrous sodium sulfate, followed by purification by silica gel column chromatography (developing solvent: toluene/heptane mixture) to give 3.2 g (yield 98%) of compound a-7 (transparent oil).

Synthesis of Compound a-8

In a 100-ml three-neck flask, 3.2 g (12.2 mmol) of compound a-7, 661 mg (1.22 mmol) of [1,1'-bis(diphenylphosphino)propane]dichloronickel, 3.55 ml (24.4 mmol) of 4,4,5,5-tetramethyl-1,3,2-dioxaborolane, 40 ml of toluene, and 5 ml of triethylamine were placed. In a nitrogen atmosphere, the resulting mixture was heated to 90° C., and stirring was performed for 6 hours. After completion of the reaction, 50 ml of water was added to the reaction solution, and the organic layer was extracted with toluene and dried over anhydrous sodium sulfate, followed by purification by silica gel column chromatography (developing solvent: toluene/heptane mixture) to give 2.2 g (yield 58.2%) of compound a-8 (transparent oil).

Synthesis of Intermediate a-14

In a 100-ml three-neck flask, 0.825 g (2.66 mmol) of compound a-8, 0.665 g (2.66 mmol) of compound a-13, 6.5 g of sodium carbonate, 30 ml of toluene, 10 ml of ethanol, and 20 ml of water were placed, and in a nitrogen atmosphere, under stirring at room temperature, 90.1 mg of tetrakis(triphenylphosphine)palladium(0) was added thereto. The resulting mixture was heated to 80° C., and stirring was performed for 5 hours. After completion of the reaction, the organic layer was extracted with toluene and dried over anhydrous sodium sulfate, followed by purification by silica gel column chromatography (developing solvent: toluene/heptane mixture) to give 0.534 g (yield 57%) of intermediate a-14 (white solid).

Synthesis of Exemplary Compound I-7

In a 100-ml three-neck flask, 0.530 g (1.50 mmol) of compound a-14, 0.638 g (1.80 mmol) of compound a-15, 6.4 g of sodium carbonate, 30 ml of toluene, 10 ml of ethanol, and 20 ml of water were placed, and in a nitrogen atmosphere, under stirring at room temperature, 86.6 mg of tetrakis(triphenylphosphine)palladium(0) was added thereto. The resulting mixture was heated to 80° C., and stirring was performed for 5 hours. After completion of the reaction, the organic layer was extracted with toluene and dried over anhydrous sodium sulfate, followed by purification by silica gel column chromatography (developing solvent: toluene/heptane mixture) to give 0.554 g (yield 74%) of exemplary compound I-7 (white solid).

By mass spectrometry, 500 as M+ of exemplary compound I-7 was confirmed.

Furthermore, the structure of exemplary compound I-7 was confirmed by $^1$H NMR measurement.

$^1$H NMR (CDCl$_3$, 400 MHz) σ (ppm): 8.72 (d, 1H), 8.69-8.66 (m, 5H), 8.14 (d, 1H), 7.94 (d, 1H), 7.81 (d, 1H), 7.76 (d, 1H), 7.72-7.65 (m, 5H), 7.61-7.57 (m, 2H), 7.52 (d, 1H), 7.49-7.41 (m, 3H), 2.46 (s, 3H)

T1 in a dilute toluene solution was measured for the following compounds. The measured T1 value for intermediate a-6 was 466 nm. The measured T1 value for exemplary compound I-7 was 471 nm. In the T1 measurement, a toluene solution (1×10$^{-4}$ mol/l) was cooled to 77 K, and the phosphorescent emission spectrum was measured at an excitation wavelength of 350 nm, and the first emission peak was used as T1. A spectrophotometer U-3010 manufactured by Hitachi was used.

Example 2

Synthesis of Exemplary Compound I-2

Exemplary compound I-2 was synthesized as in Example 1 except that, instead of compound a-15, compound a-16 shown below was used. By mass spectrometry, 465 as M+ of exemplary compound I-2 was confirmed. Furthermore, T1 in a dilute toluene solution was measured for exemplary compound I-2 as in Example 1, and the measured T1 value was 472 nm.

[Chem. 15]

a-16

Example 3

Synthesis of Exemplary Compound I-5

Exemplary compound I-5 was synthesized as in Example 1 except that, instead of compound a-15, compound a-17 shown below was used. By mass spectrometry, 449 as M+ of exemplary compound I-5 was confirmed. Furthermore, T1 in a dilute toluene solution was measured for exemplary compound I-5 as in Example 1, and the measured T1 value was 474 nm.

[Chem. 16]

a-17

Example 4

Synthesis of Exemplary Compound H-1

Exemplary compound H-1 was synthesized as in Example 1 except that, instead of compound a-13, compound a-18 shown below was used. By mass spectrometry, 485 as M+ of exemplary compound H-1 was confirmed.

[Chem. 17]

a-18

Example 5

Synthesis of Exemplary Compound D-5

Exemplary compound D-5 was synthesized as in Example 1 except that, instead of compound a-13, compound a-19 shown below was used. By mass spectrometry, 561 as M+ of exemplary compound D-5 was confirmed.

[Chem. 18]

a-19

Example 6

Synthesis of Exemplary Compound E-2

Exemplary compound E-2 was synthesized as in Example 1 except that, instead of compound a-13, compound a-18 shown below was used, and instead of compound a-15, compound a-16 was used. By mass spectrometry, 451 as M+ of exemplary compound E-2 was confirmed.

[Chem. 19]

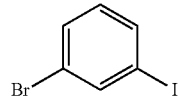
a-18

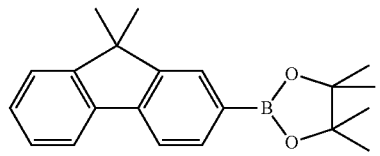
a-16

Example 7

In this example, an organic light-emitting device having a structure including an anode, a hole transport layer, a light-emitting layer, an electron transport layer, and a cathode disposed in that order on a substrate was fabricated by the method described below. A transparent conductive support substrate (ITO substrate) was prepared by forming an ITO layer, as an anode, by sputtering with a thickness of 120 nm on a glass substrate. The organic compound layers and electrode layers shown below were continuously formed on the ITO substrate by resistance-heating vacuum vapor deposition in a vacuum chamber of $10^{-5}$ Pa such that the area of the electrodes facing each other was 3 mm$^2$.

Hole transport layer (30 nm): b-1

Light-emitting layer (30 nm) host: 1-7, guest: b-2 (weight ratio 15%)

Hole/exciton blocking layer (10 nm): b-3

Electron transport layer (30 nm): b-4

Metal electrode layer 1 (1 nm): LiF

Metal electrode layer 2 (100 nm): Al

[Chem. 20]

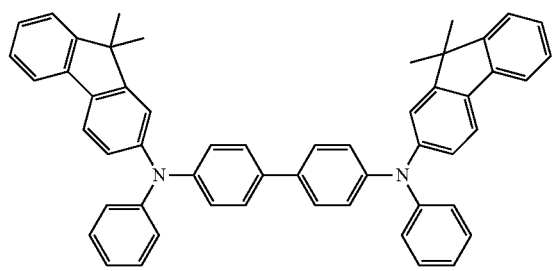
b-1

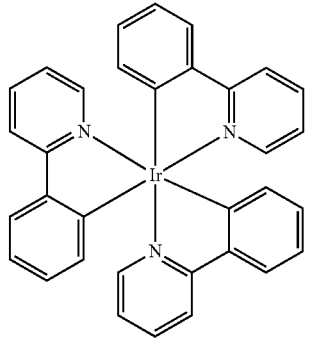
b-2

-continued

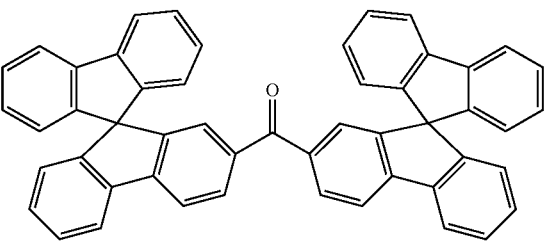
b-3

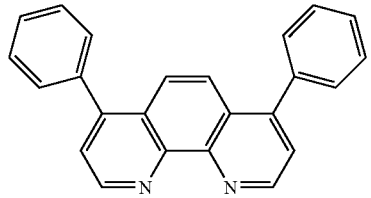
b-4

When a voltage of 5.4 V was applied to the resulting organic light-emitting device, in which the ITO electrode was set as an anode, and the Al electrode was set as a cathode, green emission with a luminous efficiency of 60.0 cd/A was observed. Furthermore, in this device, the CIE chromaticity coordinates were (x, y)=(0.34, 0.63).

Example 8

An organic light-emitting device was fabricated as in Example 7 except that, instead of exemplary compound I-7 as the host of the light-emitting layer, exemplary compound I-2 was used.

When a voltage of 5.3 V was applied to the resulting organic light-emitting device, in which the ITO electrode was set as an anode, and the Al electrode was set as a cathode, green emission with a luminous efficiency of 58.6 cd/A was observed. Furthermore, in this device, the CIE chromaticity coordinates were (x, y)=(0.34, 0.64).

As described on the basis of the embodiments and examples above, it is possible to provide a novel naphthothiophene compound having a high lowest excited triplet level (T1) of 460 to 500 nm. Furthermore, by using the novel naphthothiophene compound according to the present invention for an organic light-emitting device, it is possible to provide an organic light-emitting device having high luminous efficiency and a low driving voltage.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-099152, filed Apr. 22, 2010, which is hereby incorporated by reference herein in its entirety.

The invention claimed is:

1. A naphthothiophene compound represented by general formula [1]:

[Chem. 4]

General formula [1]

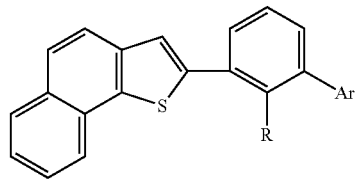

wherein, in general formula [1], Ar represents any one of a phenyl group, a phenanthryl group, a naphthyl group, a fluorenyl group, and a triphenylenyl group, and may have, as a substituent, any one kind selected from alkyl groups having 1 to 4 carbon atoms, a phenyl group, a phenanthryl group, a naphthyl group, a fluorenyl group, and a triphenylenyl group; and R represents a hydrogen atom or an alkyl group having 1 to 4 carbon atoms.

2. An organic light-emitting device comprising:
a pair of electrodes; and
an organic compound layer disposed between the pair of electrodes,
wherein the organic compound layer includes the naphthothiophene compound according to claim 1.

3. The organic light-emitting device according to claim 2, wherein the organic compound layer is a light-emitting layer, the light-emitting layer includes a host material and a guest material, and the host material is the naphthothiophene compound.

4. The organic light-emitting device according to claim 3, wherein the guest material is a phosphorescent compound.

5. A display apparatus comprising:
the organic light-emitting device according to claim 2; and
a switching device connected to the organic light-emitting device.

* * * * *